(12) United States Patent
Genov et al.

(10) Patent No.: US 7,671,198 B2
(45) Date of Patent: Mar. 2, 2010

(54) PROCESS FOR PREPARING INTERMEDIATES TO 5-HT$_4$ RECEPTOR AGONIST COMPOUNDS

(75) Inventors: Daniel Genov, San Francisco, CA (US); Junning Lee, El Granada, CA (US); Jyanwei Liu, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 375 days.

(21) Appl. No.: 11/706,732

(22) Filed: Feb. 15, 2007

(65) Prior Publication Data

US 2007/0191355 A1 Aug. 16, 2007

Related U.S. Application Data

(60) Provisional application No. 60/774,066, filed on Feb. 16, 2006.

(51) Int. Cl.
*C07D 279/10* (2006.01)
*C07D 279/12* (2006.01)
*C07D 241/04* (2006.01)
*C07D 221/18* (2006.01)
*C07D 221/22* (2006.01)
*C07D 295/00* (2006.01)

(52) U.S. Cl. .............................. 544/56; 544/358; 546/26

(58) Field of Classification Search ........................ None
See application file for complete search history.

(56) References Cited

U.S. PATENT DOCUMENTS

| 4,853,394 A | 8/1989 | King et al. |
|---|---|---|
| 5,753,673 A | 5/1998 | Ohuchi et al. |
| 6,117,882 A | 9/2000 | Schaus et al. |
| 7,329,752 B2 | 2/2008 | Long et al. |
| 2005/0197335 A1 | 9/2005 | Marquess et al. |
| 2005/0228014 A1 | 10/2005 | Marquess et al. |
| 2006/0058343 A1 | 3/2006 | Mergelsberg et al. |
| 2006/0100236 A1 | 5/2006 | Choi et al. |
| 2006/0100426 A1 | 5/2006 | Choi et al. |
| 2006/0135764 A1 | 6/2006 | Fatheree et al. |
| 2006/0183901 A1 | 8/2006 | Fatheree et al. |
| 2008/0146807 A1 | 6/2008 | Marquess et al. |

FOREIGN PATENT DOCUMENTS

| IT | 1298271 B1 | 12/1999 |
|---|---|---|
| JP | 08231544 A2 | 9/1996 |
| WO | WO 01/25236 A2 | 4/2001 |

OTHER PUBLICATIONS

Voet and Voet, Biochemistry, 1995, pp. 34-39.*
U.S. Appl. No. 11/602,888, Not yet published, Long et al.
Allegretti et al., "One-pot, new stereoselective synthesis of *endo*-tropanamine", Tetrahedron Letters 42, pp. 4257-4259 (2001).
Berdini et al., "A modified palladium catalysed reductive amination procedure", Tetrahedron 58, pp. 5669-5674 (2002).

* cited by examiner

*Primary Examiner*—James O Wilson
*Assistant Examiner*—Noble Jarrell
(74) *Attorney, Agent, or Firm*—Jeffrey A. Hagenah; Roberta P. Saxon

(57) ABSTRACT

The invention provides 8-azabicyclo[3.2.1]octyl intermediates useful for the preparation of 5-HT$_4$ receptor agonist compounds. The invention also provides processes for the preparation of such useful intermediates.

13 Claims, No Drawings

PROCESS FOR PREPARING INTERMEDIATES TO 5-HT₄ RECEPTOR AGONIST COMPOUNDS

CROSS-REFERENCE TO RELATED APPLICATIONS

This application claims the benefit of U.S. Provisional Application No. 60/774,066, filed on Feb. 16, 2006, the disclosure of which is incorporated herein by reference in its entirety.

BACKGROUND OF THE INVENTION

1. Field of the Invention

The invention is directed to 8-azabicyclo[3.2.1]octyl intermediates useful for the preparation of compounds that have demonstrated activity as 5-HT₄ receptor agonists. The invention is also directed to processes for the preparation of such useful intermediates.

2. State of the Art

Substantial research effort has been devoted in recent years to the identification of compounds that exhibit agonist activity at 5-HT₄ receptors. Such compounds are expected to be useful as therapeutic agents for the treatment of disorders of reduced motility of the gastrointestinal tract. Commonly-assigned US 2005/0197335 and US 2005/0228014, for example, disclose novel indazole-carboxamide-8-azabicyclo-[3.2.1]octane and quinolinone-carboxamide-8-azabicyclo[3.2.1]octane compounds, respectively, as 5-HT₄ receptor agonists.

Efficient processes for the preparation of compounds including the 8-azabicyclo-[3.2.1]octane group would be advantageous for providing new gastrointestinal motility agents.

SUMMARY OF THE INVENTION

The present invention provides compounds containing the 8-azabicyclo-[3.2.1]-octane group which are useful intermediates for the preparation of 5-HT₄ receptor agonists and processes for the preparation of such useful intermediates.

Accordingly, the invention provides a compound of formula (I):

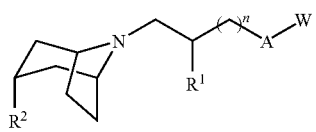
(I)

wherein:

$R^1$ is selected from hydrogen, —OH and —OP$^1$, wherein P$^1$ is a hydroxy-protecting group;

$R^2$ is =O or —NR$^a$R$^b$, wherein R$^a$ and R$^b$ are independently hydrogen or P$^2$, wherein P$^2$ is an amino-protecting group;

A is selected from —OC(O)—, —S(O)₂—, and a covalent bond;

W is selected from —N(R$^3$)C(O)R$^4$, —N(R$^5$)S(O)₂R$^6$, and a moiety of formula (a):

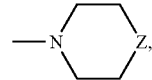
(a)

wherein Z is selected from NC(O)R$^4$, NS(O)₂R$^6$, S(O)₂, NH, and NP$^2$;

$R^3$, $R^4$, $R^5$, and $R^6$ are independently C$_{1-3}$alkyl; and n is 0 or 1;

or a salt thereof.

The invention further provides a compound of formula (Ia):

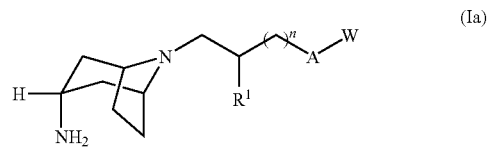
(Ia)

or a salt thereof, and processes for the preparation thereof.

In addition, the invention provides a compound of formula (Ib):

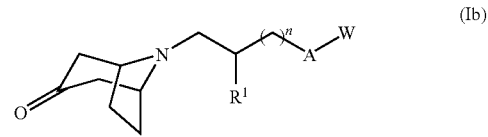
(Ib)

or a salt thereof, and processes for the preparation thereof.

DETAILED DESCRIPTION OF THE INVENTION

The following substituents and values are intended to provide representative examples of various aspects of this invention. These representative values are intended to further define such aspects and are not intended to exclude other values or limit the scope of the invention.

In a specific aspect of the invention, R$^1$ is selected from hydrogen, —OH, and —OP$^1$, wherein P$^1$ is a hydroxy-protecting group.

In other specific aspects, R$^1$ is hydrogen; or R is —OH or —OP$^1$.

In a specific aspect of the invention, R$^2$ is =O or —NR$^a$R$^b$, wherein R$^a$ and R$^b$ are independently hydrogen or an amino-protecting group P$^2$.

In another specific aspect, R$^2$ is =O.

In another specific aspect, R$^2$ is —NH$_2$.

In yet other specific aspects, R$^2$ is —NHR$^b$ wherein R$^b$ is benzyl; or R$^2$ is —NR$^a$R$^b$ wherein R$^a$ and R$^b$ are both benzyl.

In a specific aspect, A is selected from —OC(O)—, —S(O)₂—, and a covalent bond.

In another specific aspect, A is a covalent bond.

In a specific aspect, W is selected from —N(R$^3$)C(O)R$^4$, —N(R$^5$)S(O)₂R$^6$, and a moiety of formula (a):

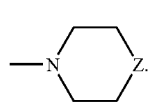
(a)

In another specific aspect, W is —N(R³)C(O)R⁴ or —N(R⁵)S(O)₂R⁶, wherein R³, R⁴, R⁵, and R⁶ are independently $C_{1-3}$alkyl.

In yet another specific aspect, W is —N(R³)C(O)R⁴ or —N(R⁵)S(O)₂R⁶, wherein R³, R⁴, R⁵, and R⁶ are methyl.

In a further specific aspect, W is a moiety of formula (a) wherein Z is selected from NC(O)R⁴, NS(O)₂R⁶, S(O)₂, NH, and NP², wherein R⁴ and R⁶ are independently $C_{1-3}$alkyl.

In yet another aspect, W is a moiety of formula (a) wherein Z is selected from NC(O)R⁴, NS(O)₂R⁶, and S(O)₂, wherein R⁴ and R⁶ are methyl.

In further aspects, W is a moiety of formula (a), wherein Z is NH or NP²; or Z is NH.

In a specific aspect, n is 0.

In another specific aspect, n is 1.

In one aspect of the invention, n is 0 and R¹ is hydrogen.

In another aspect of the invention. n is 1 and R¹ is —OH or —OP¹.

Definitions

When describing the compounds and methods of the invention, the following terms have the following meanings, unless otherwise indicated.

The term "alkyl" means a monovalent saturated hydrocarbon group which may be linear or branched, for example, methyl, ethyl, n-propyl (n-Pr), and isopropyl (i-Pr).

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), diphenylmethyl, and 1,1-di-(4'-methoxyphenyl) methyl; silyl groups, such as trimethylsilyl (TMS) and tert-butyl-dimethylsilyl (TBDMS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The use of protecting groups for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

The chemical naming conventions used herein are illustrated for the compound of Example 1:

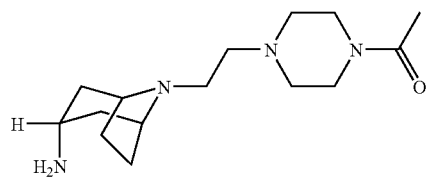

which is designated 1-{4-[2-((1R,3R,5S)-3-amino-8-azabicyclo[3.2.1 ]oct-8-yl)ethyl]piperazin-1-yl}ethanone using the commercially-available AutoNom software (MDL Information Systems, GmbH, Frankfurt, Germany). The designation (1S,3R,5R) describes the relative orientation of the bonds associated with the bicyclic ring system. The compound is alternatively denoted as 1-{4-[2-(3-endo-amino-8-azabicyclo[3.2.1]oct-8-yl)ethyl]piperazin-1-yl}ethanone. All of the compounds of the invention in which R² is —NRᵃRᵇ are in the endo configuration.

Synthetic Procedures

In one method of synthesis, a tropanamine of formula (Ia)

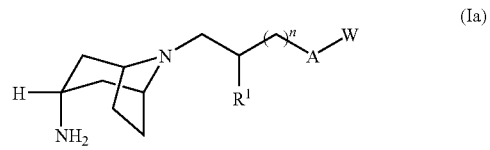
(Ia)

is prepared by reductive amination of a tropanone of formula (Ib):

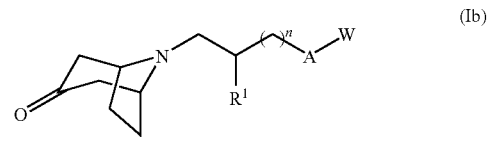
(Ib)

where the variables R¹, A, W, and n are as defined above.

Typically compound (Ib) is reacted with a large excess, between about 15 and about 25 equivalents, of ammonium formate in an inert diluent, such as methanol or ethanol. A small amount of water, about 0.1 to about 0.2 volume equivalents with respect to methanol or ethanol, is typically included in the inert diluent. The reaction, which is conducted in the presence of a transition metal catalyst, typically palladium or palladium hydroxide on carbon, provides intermediate (Ia) in the endo configuration with high stereospecificity. Typically the ratio of endo to exo configuration of the product (Ia) is greater than about 99:1. The reaction is typically conducted at a temperature between about 10 and about 30° C. for about 12 to about 72 hours or until the reaction is substantially complete. The product can be purified by conventional extraction procedures.

Alternatively, tropanamine (Ia) can be prepared from tropanone (Ib) according to the two step process illustrated in Scheme A:

Scheme A

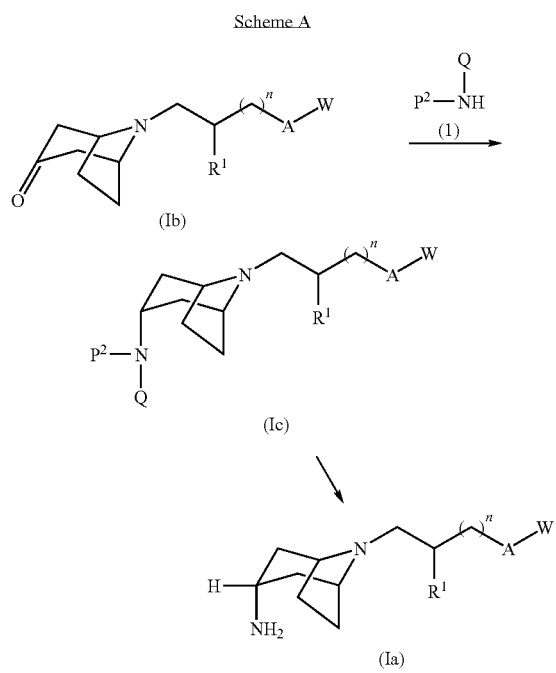

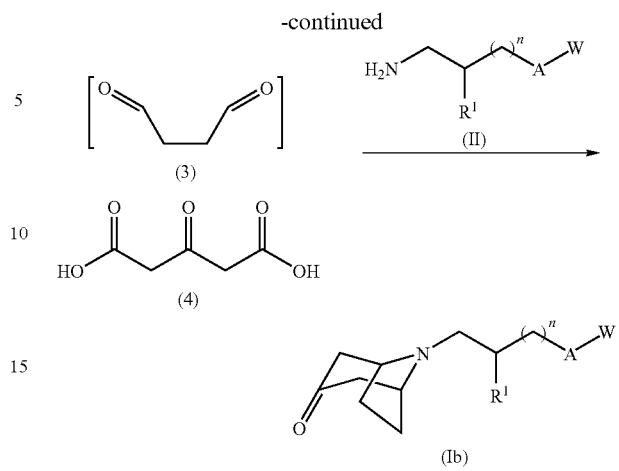

where Q represent hydrogen or an amino-protecting group $P^2$.

According to the process of Scheme A, tropanone (Ib) is first contacted with between about 1 and about 1.5 equivalents of a protected amine $NHP^2Q$ (1) in the presence of between about 1 and about 1.5 equivalents of a reducing agent and about 0.5 equivalents of acetic acid to provide the protected tropanamine (Ic). The protecting group $P^2$ is advantageously selected as benzyl or diphenylmethyl. Useful protected amines (1) include benzylamine, dibenzylamine, and diphenylmethylamine. Dichloromethane is typically used as the inert diluent for this reaction. Alternative diluents include ethers such as dimethoxyethane. The reaction is typically conducted at a temperature between about 10 and about 30° C. for about 12 to about 72 hours or until the reaction is substantially complete. Typical reducing agents include sodium triacetoxyborohydride, sodium borohydride, and sodium cyanoborohydride.

In a second step, the protected tropanamine (Ic) is deprotected by conventional procedures. For example, when $P^2$ is benzyl or diphenylmethyl, the protecting group(s) can be removed by reduction using, for example, hydrogen or ammonium formate and a group VIII metal catalyst, such as palladium on carbon, to provide compound (Ia).

The tropanone intermediate (Ib) is advantageously prepared from readily available starting materials according to the process of Scheme B where the bicyclic ring formation and amine coupling are accomplished in the same reaction step.

Scheme B

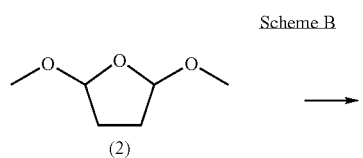

As shown in Scheme B, 2,5-dimethoxytetrahydrofuran (2), which has been hydrolyzed to succinaldehyde (3) in an aqueous acidic environment is contacted with between about 1 and about 1.5 equivalents of the amine (II) and a slight excess, for example, about 1.1 equivalents of 3-oxopentanedioic acid (4), commonly 1,3-acetonedicarboxylic acid. The reaction is conducted in the presence of an excess, for example between about 3 and about 6 equivalents, of a buffering agent such as sodium acetate or sodium hydrogen phosphate, to maintain the pH of the reaction mixture between about 4 and about 6. The reaction mixture is typically heated to between about 40 and about 50° C. for about 1 to about 4 hours or until the reaction is substantially complete. The product (Ib) is extracted by conventional procedures.

Compounds of formula (Ib) in which W is a moiety of formula (a)

wherein Z is $NC(O)R^4$ or $NS(O)_2R^6$ can alternatively be prepared from compounds of formula (Ib) in which W is a moiety of formula (a) wherein Z is NH, i.e. compounds wherein W is piperazinyl, by reactions with conventional reagents under standard conditions. For example, when Z is $NC(O)CH_3$, acetic anhydride may be used as the reagent for the acylating reaction. When Z is $NS(O)_2CH_3$, methanesulfonyl chloride may be used to prepare a compound of formula (Ib) from a compound of formula (Ib) in which W is piperazinyl.

The amines of formula (II) are either commercially available or can be prepared from commonly available starting materials by procedures known to those skilled in the art. Further details regarding specific reaction conditions and other procedures for preparing a compound of formula (I) or intermediates thereto are described in the examples below.

Accordingly, in a method aspect, the invention provides a process for preparing a compound of formula (Ia) or a salt thereof, the process comprising:

(a) reacting a compound of formula (1b) with at least 15 equivalents of ammonium formate in the presence of a transition metal catalyst; or (b) reacting a compound of formula (1b) with a protected amine of formula NHP²Q in the presence of a reducing agent, followed by removing the protecting group or groups;

to provide a compound of formula (Ia) or a salt thereof.

In a second method aspect, the invention provides a process for preparing a compound of formula (Ib) or a salt thereof, the process comprising:

(a) hydrolyzing 2,5-dimethoxytetrahydrofuran in an aqueous acidic medium; and (b) reacting the product of step (a) with a compound of formula (II) and 3-oxopentanedioic acid in the presence of a buffering agent;

to provide a compound of formula (Ib) or a salt thereof.

The compounds of the invention are useful intermediates for the preparation of 5-$HT_4$ receptor agonists. For example, compounds of formula (Ia) can be reacted with 1-isopropyl-1H-indazole-3-carboxylic acid to provide indazole-carboxamide 5-$HT_4$ receptor agonist compounds, for example the compounds described in US 2005/0197335, US 2006/0183901 or intermediates thereto.

Compounds which are 5-$HT_4$ receptor agonists are expected to be useful for treating medical conditions mediated by 5-$HT_4$ receptors or associated with 5-$HT_4$ receptor activity, i.e. medical conditions which are ameliorated by treatment with a 5-$HT_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, diabetic and idiopathic gastropathy, post-operative ileus, intestinal pseudo-obstruction, and drug-induced delayed transit. In addition, it has been suggested that some 5-$HT_4$ receptor agonist compounds may be used in the treatment of central nervous system disorders including cognitive disorders, behavioral disorders, mood disorders, and disorders of control of autonomic function.

In particular, such compounds are expected to increase motility of the gastrointestinal (GI) tract and thus are expected to be useful for treating disorders of the GI tract caused by reduced motility in mammals, including humans. These GI motility disorders include, by way of illustration, chronic constipation, constipation-predominant irritable bowel syndrome (C-IBS), diabetic and idiopathic gastroparesis, and functional dyspepsia.

EXAMPLES

The following synthetic examples are offered to illustrate the invention, and are not to be construed in any way as limiting the scope of the invention. Abbreviations not defined below have their generally accepted meanings.

Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), liquid chromatography mass spectroscopy (LCMS), and gas liquid chromatography (GC), the details of which are given below and separately in specific examples of reactions. Reaction mixtures were worked up as described specifically in each reaction; commonly they were purified by extraction and other purification methods such as temperature-, and solvent-dependent crystallization, and precipitation. Characterization of reaction products was routinely carried out by mass and $^1$H-NMR spectrometry. For NMR measurement, samples were dissolved in deuterated solvent ($D_2O$, $CDCl_3$, or DMSO-$d_6$), and $^1$H-NMR spectra were acquired with a Varian Gemini 2000 instrument (300 MHz) under standard observation conditions.

General Protocol for Analytical HPLC

Crude compounds were dissolved in 50% MeCN/$H_2O$ (with 0.1% TFA) at 0.5-1.0 mg/mL concentration, and analyzed using the following conditions:

Column: Zorbax Bonus-RP (5.0 μm of particle size, 4.6× 150 mm)

Flow rate: 2.0 mL/min

Detector wavelength: 214, 254, and 280 nm.

Example 1

Synthesis of (1R,5S)-8-[2-(4-acetylpiperazin-1-yl) ethyl]-8-azabicyclo[3.2.1]octan-3-one Concentrated hydrochloric acid (50 mL) was added to a solution of 2,5-dimethoxy tetrahydrofuran (490.2 mL, 3.78 mol) in water (1200 mL). The resulting yellow solution was stirred at about 70-72° C. for about 2 h.

1-(2-Aminoethyl)piperazine (546.4 mL, 4.16 mol, 1.1 equiv.) was added to a solution of sodium acetate (1225.5 g) dissolved in water (3700 mL) at 15° C. Concentrated hydrochloric acid (350 mL) was added slowly keeping the internal temperature below 25° C. After cooling the mixture to 15° C., 3-oxopentanedioic acid (607.8 g, 4.16 mol) was added, and the solution temperature again cooled to 15° C. The aqueous yellow solution prepared above was added slowly over about 10 min, and the resulting yellow mixture was stirred at about 20° C. for about 30 min until carbon dioxide evolution slowed. The mixture was stirred at 40-45° C. for 2 h and the color of the reaction mixture turned dark brown.

The mixture was cooled to about 15° C. Aqueous sodium hydroxide (50%, ~470 mL) was added in portions, keeping the temperature below 25°, until pH 13 was reached. Sodium chloride (600 g) was added and the mixture was stirred to complete dissolution. The product was extracted with dichloromethane (DCM) (1×2000 mL, 2×1500 mL). The combined organic phases were dried, filtered and the solution concentrated to 2500 mL.

The concentrated solution was cooled to 15° C. and acetic anhydride (500 mL) was added slowly, keeping the temperature below 25° C. The solution was stirred for 30 min and water (1500 mL) was added at 15° C. The mixture was stirred for 10 min, then acidified to pH 1 using 1M hydrochloric acid.

The DCM and aqueous phases were separated. Gas chromatography analysis revealed that there was no remaining product in the DCM phase. The aqueous phase was basefied to pH 14 by the portionwise addition of aqueous phase sodium hydroxide (50% in water, about 500 mL), keeping the internal temperature below 25° C. The product was extracted with DCM (3×1500 mL), and the collected organic phases (dark brown) were combined, dried, filtered through celite, and distilled to produce the title compound as a viscous brown oil (650 g, 94% purity by gas chromatography). $^1$H NMR ($CDCl_3$, 300 MHz) δ ppm: 3.65 (t, 2H), 3.56 (m, 2H), 3.48 (t, 2H), 2.78-2.47 (m, 10H), 2.23-2.02 (m, 4H), 2.10 (m, 3H), 1.61(m, 2H); $^{13}$C NMR ($CDCl_3$, 75MHz) δ ppm: 209.81, 168.90, 59.10, 57.83, 53.83, 53.22, 48.01, 47.40, 46.19, 41.30, 27.80, 21.28.

Example 2

Synthesis of 1-{4-[2-((1R,3R,5S)-3-amino-8-azabicyclo[3.2.1]oct-8-yl)ethyl]piperazin-1-yl}ethanone (1R,5S)-8-[2-(4-Acetylpiperazin-1-yl)ethyl]-8-azabicyclo[3.2.1]octan-3-one, (31.0 g, 0.111 mol), prepared as described in Example 1, was dissolved in isopropyl alcohol (100 mL) at room temperature. The solution was heated to about 60° C. and 1,5-naphthalenedisulfonic acid tetrahydrate dissolved in isopropyl alcohol (70 mL) was added slowly over 1 h with stirring. After completion of the addition of the acid, the addition funnel was washed with isopropyl alcohol (50 mL). The mixture was stirred at about 60° C. for 1 h, cooled to room temperature, then stirred for 15 h. The mixture was filtered, and the resulting cake was washed with isopropyl alcohol (2×50 mL) and kept on the filter for 30 min. The product was then transferred to a flask and dried under high vacuum for 24 h to produce (1R,5S)-8-[2-(4-acetylpiperazin-1-yl)ethyl]-8-azabicyclo[3.2.1]octan-3-one 1,5-naphthalene-disulfonic salt as a beige crystalline nonhydroscopic material (51.7 g). $^1$H NMR (D$_2$O, 300 MHz) δ ppm: 8.84 (d, 2H), 8.20 (d, 2H), 7.73 (t, 2H), 4.23 (br s, 2H), 3.74 (m, 4H), 3.62 (s, 4H), 3.32 (m, 4H), 3.32-2.98 (m, 2H), 2.58 (d, 2H), 2.27 (m, 2H), 2.07 (s, 3H), 1.97 (d, 2H).

A stirred solution of (1R,5S)-8-[2-(4-acetylpiperazin-1-yl)ethyl]-8-azabicyclo-[3.2.1]-octan-3-one 1,5-naphthalene-disulfonic salt (51.6 g) in water (500 mL), cooled to 5° C., was basified to pH 14 using aqueous sodium hydroxide (50%), keeping the temperature below 15° C. DCM (300 mL) was added and the emulsion formed was filtered through celite. The layers were separated and the aqueous layer was washed with DCM (3×100 mL). The combined organic phases were dried for 24 h to produce (1R,5S)-8-[2-(4-acetylpiperazin-1-yl)ethyl]-8-azabicyclo[3.2.1]octan-3-one (23.3 g, 93% yield based on the salt).

(1R,5S)-8-[2-(4-Acetylpiperazin-1-yl)ethyl]-8-azabicyclo[3.2.1]octan-3-one (58.2 g, 0.209 mol) was dissolved in methanol (300 mL) at room temperature. To this solution, ammonium formate (263.1 g, 4.17 mol, 20 equiv.) was added, followed by the addition of methanol (100 mL) and water (85 mL). Palladium (wetted 10% palladium on activated carbon, 58 g) was added to the mixture, followed by the addition of methanol (150 mL). The reaction mixture was stirred at room temperature for about 20 h, until gas chromatography analysis revealed complete conversion of the ketone. The reaction mixture was filtered through celite, the resulting cake was washed with methanol (about 700 mL), and the solvent removed. The residue was dissolved in water (300 mL), the solution was cooled to 5° C., and the solution basified to pH 14 using 50% sodium hydroxide. The solution was saturated with sodium chloride and the product was extracted with DCM (400 mL). The aqueous phase was washed with DCM (3×150 mL). The combined organic fractions were dried for about 24 h under high vacuum to produce the title compound as a viscous light brown oil (43 g, 91% purity by gas chromatography). $^1$H NMR (CDCl$_3$, 300MHz) δ ppm: 3.61 (t, 2H), 3.46 (t, 2H), 3.23 (t, 1H), 3.18 (m, 2H), 2.47 (m, 8H), 2.14-1.93 (m, 6H), 2.08 (s, 3H), 1.41 (d, 2H), 1.40 (br s, 2H); $^{13}$C NMR (CDCl$_3$, 75MHz) δ ppm: 168.79, 58.87, 57.36, 53.69, 53.35, 53.12, 49.41, 46.13, 42.65, 41.22, 38.47, 26.39, 21.22.

Example 3

Synthesis of 1-{4-[2-((1R,3R,5S)-3-benzylamino-8-azabicyclo-[3.2.1]oct-8-yl)ethyl]piperazin-1-yl}-ethanone (1R,5S)-8-[2-(4-Acetylpiperazin-1-yl)ethyl]-8-azabicyclo[3.2.1]octan-3-one (9.5 g, 0.034 mol) was dissolved in DCM (200 mL) at room temperature. To this solution benzylamine (4.49 g, 0.041 mol, 1.2 equiv) and acetic acid (1.02 g, 0.017 mol, 0.5 equiv) were added, followed by the in situ addition of sodium triacetoxy borohydride (14.42 g, 0.068 mol, 2 equiv). The mixture was stirred at room temperature for 24 h, cooled to about 10° C. with an ice bath and 5M sodium hydroxide (200 mL) was added, keeping the temperature below 20° C. The two phases were separated and the organic phase was dried (Na$_2$SO$_4$). After removal of the solvent by distillation, the crude product was dried under high vacuum for 48 h to obtain 11.2 g (89%) of the title compound as brown oil. $^1$H NMR (CDCl$_3$, 300 MHz) δ ppm: 7.31 (m, 5H), 3.73 (s, 2H), 3.61 (t, 2H), 3.46 (t, 2H), 3.17 (m, 2H), 2.94 (t, 1H), 2.52-1.89 (m, 14H), 2.08 (s, 3H), 1.56 (d, 2H); $^{13}$C NMR (CDCl$_3$, 75 MHz) δ ppm: 168.71, 140.94, 128.14, 127.86, 126.58, 58.79, 57.72, 53.69, 52.43, 49.61, 46.10, 41.20, 35.88, 26.51, 21.18.

Example 4

Synthesis of 1-{4-[2-((1R,3R,5S)-3-amino-8-azabicyclo[3.2.1]oct-8-yl)ethyl]piperazin-1-yl}ethanone (via an alternate route)

1-{4-[2-((1R,3R,5S)-3-Benzylamino-8-azabicyclo[3.2.1]oct-8-yl)ethyl]piperazin-1-yl}-ethanone, the product of Example 3, (17.6 g, 0.0475 mol) was dissolved in methanol (250 mL). Acetic acid (8.55 g, 0.142 mol, 3 equiv) was added followed by the addition of the palladium catalyst (wetted 10% palladium on activated carbon, 3.6 g, 20 wt %). The hydrogenation was carried out using 40 psi H$_2$ pressure for 24 h at room temperature. The mixture was filtered through celite and the solvent was removed by distillation. The residue was dissolved in water (200 mL) and the pH was adjusted to 14 with 50% sodium hydroxide. The aqueous solution was saturated with sodium chloride and the product was extracted with DCM. The organic phase was dried over Na$_2$SO$_4$. After the removal of the solvent by distillation and further drying under high vacuum for 24 h, the title compound was obtained as light brown oil (11.3 g, 85%). The $^1$H NMR of the title compound matched that of the compound reported in Example 2.

Example 5

Synthesis of 1-(4-{2-[(1R,3R,5S)-3-(Benzhydryl-amino)-8-aza-bicyclo[3.2.1]oct-8-yl]ethyl}-piperazin-1-yl)ethanone Following the process described in Example 5, except replacing benzylamine of Example 3 with 1,1-diphenyl-methanamine, the title compound was obtained.

Example 6

Synthesis of 1-{4-[2-((1R,3R,5S)-3-amino-8-azabicyclo[3.2.1]oct-8-yl)ethyl]piperazin-1-yl}ethanone (via a second alternate route)

Following the process described in Example 4, except replacing 1-{4-[2-((1R,3R,5S)-3-benzylamino-8-azabicyclo[3.2.1]oct-8-yl)ethyl]piperazin-1-yl}-ethanone with 1-(4-{2-[(1R,3R,5S)-3-(benzhydryl-amino)-8-aza-bicyclo[3.2.1]oct-8-yl]ethyl}-piperazin-1-yl)ethanone, the title compound was obtained.

Example 7

Synthesis of N-{(2R)-2-hydroxy-3-[(1R,5S)-3-oxo-8-azabicyclo-[3.2.1]oct-8-yl]propyl}-N-methyl-methanesulfonamide a. Preparation of N-methyl-N—[(S)-2-oxiran-2-ylmethyl]methanesulfonamide A 12 L flask was charged with water (1 L) followed by the addition sodium hydroxide (50% in water, 146.81 g, 1.835 mol). The beaker containing sodium hydroxide was washed with water (2×500 mL) and the washings were added to the flask. The mixture was stirred at room temperature for 10 min and cooled to ~8° C. (N-methyl)-methanesulfonamide (200.2 g, 1.835 mol) in water (500 mL) was added over 5 min. The mixture was stirred for 1 h at ~4° C. and (S)-2-chloromethyloxirane (339.6 g, 3.67 mol) was added. The mixture was stirred for 20 h at 3-4° C. Dichloromethane (2 L) was added and the mixture was stirred for 30 min at 5-10° C. The two layers were allowed to separate over 10 min and collected. The organic layer (~2.5 L) was added back to the 12 L flask and washed with 1 M phosphoric acid (800 mL) and brine (800 mL). Dichloromethane was removed by rotary evaporation. Toluene (400 mL) was added to the crude product, then removed by rotary evaporation. After three additional cycles of the toluene process, the title intermediate was obtained (228.2 g).

b. Preparation of N—((R)-3-amino-2-methylpropyl)-N-methylmethanesulfonamide

N-methyl-N-[(S)-2-oxiran-2-ylmethyl]methanesulfonamide is dissolved in ethanol and benzyl amine (1-1.1 equiv) is added to the solution. (Alternatively, N-methyl-N-[(S)-2-oxiran-2-ylmethyl]methanesulfonamide is dissolved in ethanol and 1,1-diphenyl-methanamine (1-1.1 equiv) is added to the solution.) The mixture is refluxed until completion of the reaction. The product is isolated and extracted.

The product of the previous step is deprotected by hydrogenation with $H_2$ gas in methanol in the presence of acetic acid (0.9-1.1 equiv) using a palladium on carbon catalyst. After removal of the catalyst by filtration, the title intermediate is isolated and extracted.

c. Synthesis of N-{(2R)-2-hydroxy-3-[(1R,5S)-3-oxo-8-azabicyclo[3.2.1]oct-8-yl]-propyl}-N-methylmethanesulfonamide Following the process described in Example 1, except replacing 1-(2-aminoethyl)-piperazine of Example 1 with N-((R)-3-amino-2-methylpropyl)-N-methylmethane-sulfonamide, the title compound is obtained.

Example 8

Synthesis of N-{(2R)-2-hydroxy-3-[(1R,5S)-3-oxo-8-azabicyclo-[3.2.1]oct-8-yl]propyl}-N-methyl-methanesulfonamide (via an alternative route)

a. Preparation of N—((R)-3-amino-2-methylpropyl)-N-methylmethanesulfonamide

N-methyl-N-[(S)-2-oxiran-2-ylmethyl]methanesulfonamide is dissolved in dimethylformamide and sodium azide (1-1.1 equiv) is added to the solution. The mixture is refluxed until completion of the reaction. The product is isolated by the addition of brine to the solution and extraction with an ether solvent.

The product of the previous step is deprotected by hydrogenation with $H_2$ gas in methanol in the presence of acetic acid (0.9-1.1 equiv) using a palladium catalyst. After removal of the catalyst by filtration, the title intermediate is isolated and extracted.

b. Synthesis of N-{(2R)-2-hydroxy-3-[(1R,5S)-3-oxo-8-azabicyclo[3.2.1]oct-8-yl]-propyl}-N-methylmethanesulfonamide Following the process described in Example 1, except replacing 1-(2-aminoethyl)-piperazine of Example 1 with N-((R)-3)-3-amino-2-methylpropyl)-N-methylmethane-sulfonamide, prepared by the process of the previous step, the title compound is obtained.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modification are intended to be within the scope of the claims appended hereto. Additionally, all publications, patents, and patent documents cited hereinabove are incorporated by reference herein in full, as though individually incorporated by reference.

What is claimed is:

1. A compound of formula (Ib):

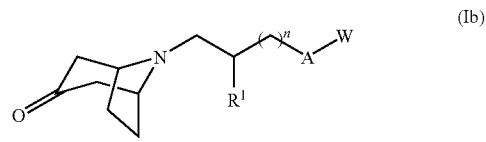

wherein:
$R^1$ is selected from hydrogen, —OH, and —$OP^1$, wherein $P^1$ is a hydroxy-protecting group;
A is selected from —OC(O)—, —S(O)$_2$—, and a covalent bond;
W is selected from —N($R^3$)C(O)$R^4$, —N($R^5$)S(O)$_2$$R^6$, and a moiety of formula (a):

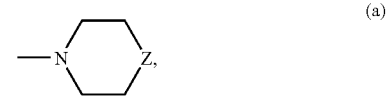

wherein Z is selected from NC(O)$R^4$, NS(O)$_2$ $R^6$, S(O)$_2$, NH, and $NP^2$;
$R^3$, $R^4$, $R^5$, and $R^6$ are independently $C_{1-3}$alkyl;
$P^2$ is an amino-protecting group; and
n is 0 or 1;
or a salt thereof.

2. The compound of claim 1 wherein n is 0 and $R^1$ is hydrogen.

3. The compound of claim 1 wherein n is 1 and $R^1$ is —OH or —$OP^1$.

4. The compound of claim 1 wherein A is a covalent bond.

5. The compound of claim 1 wherein W is a moiety of formula (a).

6. The compound of claim 5 wherein Z is selected from NC(O)$R^4$, NS(O)$_2$$R^6$, and S(O)$_2$ and $R^4$ and $R^6$ are each methyl.

7. The compound of claim 5 wherein Z is NH.

8. The compound of claim 1 wherein W is —N($R^3$)C(O) $R^4$, or —N($R^5$)S(O)$_2$$R^6$.

9. A process for preparing a compound of formula (Ib) or a salt thereof:

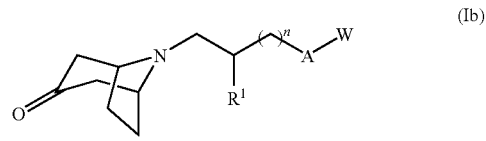

wherein $R^1$, A, W, and n are defined as in claim 1, the process comprising:
(a) hydrolyzing 2,5-dimethoxytetrahydrofuran in an aqueous acidic medium; and
(b) reacting the product of step (a) with a compound of formula (II):

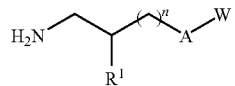

(II)

and 3-oxopentanedioic acid in the presence of a buffering agent in a reaction mixture;
to provide a compound of formula (Ib) or a salt thereof.

10. The process of claim 9 wherein the buffering agent is present in an amount sufficient to maintain the pH of the reaction mixture between 4 and 6.

11. A process for preparing a compound of formula (Ia) or a salt thereof:

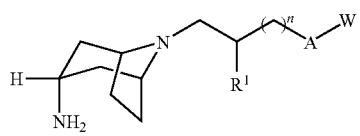

(Ia)

wherein $R^1$, A, W, and n are defined as in claim 1, the process comprising:
(a) reacting a compound of formula (Ib):

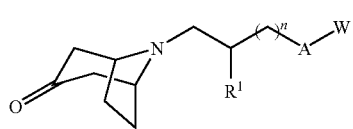

(Ib)

with at least 15 equivalents of ammonium formate in the presence of a transition metal catalyst; or
(b) reacting a compound of formula (Ib) with a protected amine of formula $NHP^2Q$, wherein Q is hydrogen or $P^2$ and $P^2$ is an amino-protecting group, in the presence of a reducing agent, followed by removing the protecting group or groups;
to provide a compound of formula (Ia) or a salt thereof.

12. The process of claim 11 wherein the process comprises step (a).

13. The process of claim 12, wherein the product of formula (Ia) has an endo to exo ratio of greater than 99:1.

* * * * *